US005472702A

United States Patent [19]

Muth et al.

[11] Patent Number: 5,472,702
[45] Date of Patent: Dec. 5, 1995

[54] STERILIZATION OF GROWTH FACTORS

[75] Inventors: Ross R. Muth, Brookfield; Matthew E. Hermes, Easton; Donald S. Kaplan, Weston, all of Conn.

[73] Assignee: United States Surgical Corporation, Norwalk, Conn.

[21] Appl. No.: 232,310

[22] Filed: Apr. 25, 1994

Related U.S. Application Data

[63] Continuation of Ser. No. 970,597, Oct. 30, 1992, abandoned, which is a continuation of Ser. No. 801,620, Dec. 3, 1991, abandoned, which is a continuation of Ser. No. 640,910, Jan. 11, 1991, abandoned, which is a continuation-in-part of Ser. No. 395,476, Aug. 18, 1989, abandoned, which is a continuation-in-part of Ser. No. 529,740, May 22, 1990, Pat. No. 5,037,429, which is a continuation of Ser. No. 89,735, Aug. 26, 1987, abandoned, and a continuation-in-part of Ser. No. 221,308, Jul. 19, 1988, Pat. No. 5,051,272, and a continuation-in-part of Ser. No. 397,405, Aug. 23, 1989, abandoned.

[51] Int. Cl.$^6$ ..................................................... A61L 2/20
[52] U.S. Cl. ........................... 424/422; 424/423; 424/443; 424/444; 424/445; 424/446; 424/447; 422/34; 623/1; 623/11; 606/139; 606/151; 606/233
[58] Field of Search ............................ 424/422, 423, 424/443–447; 422/34; 530/399; 623/3, 7, 11, 66, 1; 514/21; 606/151, 139, 228

[56] References Cited

U.S. PATENT DOCUMENTS

| | | | |
|---|---|---|---|
| 3,815,315 | 6/1974 | Glick | 53/21 FC |
| 3,883,497 | 5/1975 | Gregory et al. | 260/112 R |
| 3,917,824 | 11/1975 | Camble et al. | 424/177 |
| 3,948,875 | 4/1976 | Cohen et al. | 260/112 R |
| 3,991,766 | 11/1976 | Schmitt et al. | 128/335.5 |
| 4,148,664 | 4/1979 | Cruz | 106/161 |
| 4,179,337 | 12/1979 | Davis et al. | 435/181 |
| 4,186,192 | 1/1980 | Lundblad | 424/85 |
| 4,338,397 | 7/1982 | Gilbert et al. | 435/68 |
| 4,373,519 | 2/1983 | Errede et al. | 128/156 |
| 4,418,691 | 12/1983 | Yannas et al. | 128/156 |
| 4,432,964 | 2/1984 | Shell | 424/14 |

(List continued on next page.)

FOREIGN PATENT DOCUMENTS

| | | |
|---|---|---|
| 0046039 | 2/1982 | European Pat. Off. . |
| 0128733 | 12/1984 | European Pat. Off. . |
| 0131868 | 1/1985 | European Pat. Off. . |
| 0136490 | 4/1985 | European Pat. Off. . |
| 0147178 | 7/1985 | European Pat. Off. . |
| 0150572 | 8/1985 | European Pat. Off. . |
| 0177915 | 4/1986 | European Pat. Off. . |
| 0267015 | 5/1988 | European Pat. Off. . |
| 2092155A | 8/1982 | United Kingdom . |
| 2162851A | 2/1986 | United Kingdom . |
| 2172890 | 10/1986 | United Kingdom . |
| WO83/04030 | 11/1983 | WIPO . |
| WO85/00369 | 1/1985 | WIPO . |
| 8501284 | 3/1985 | WIPO . |
| 8602271 | 4/1986 | WIPO . |

OTHER PUBLICATIONS

Brown et al., "Acceleration of Tensile Strength of Incisions Treated with EGF and TGF–beta", Ann. Surg., p. 788 et seq. (Dec. 1988).

Barbul et al., eds., "Growth Factors and Other Aspects of Wound Healing/Biological and Clinical Implications", Proceedings of the Second International Symposium on Tissue Repair, Tarpon Springs, Fla., May 13–17, 1987 (Alan R. Liss, Inc., N.Y.).

Biochemistry 1981, 20, 4667–4676.

Biochemistry 1981, 20, 4677–4686.

Lynch et al., "Growth Factors in Wound Healing", J. Clin. Invest., vol. 84, Aug. 1989, 640–646.

*Primary Examiner*—Gollamudi S. Kishore

[57] ABSTRACT

A human growth factor (HGF), a human growth factor-containing composition or a medical or surgical device such as a wound dressing or suture filled with a human growth factor-containing composition is sterilized employing an ethylene oxide gaseous sterilizant.

3 Claims, No Drawings

U.S. PATENT DOCUMENTS

| | | | |
|---|---|---|---|
| 4,439,181 | 3/1984 | Blacksbear et al. | 604/56 |
| 4,528,186 | 7/1985 | Nishimura et al. | 424/99 |
| 4,570,629 | 2/1986 | Widra | 128/156 |
| 4,581,028 | 4/1986 | Fox et al. | 623/2 |
| 4,621,052 | 11/1986 | Sugimoto | 435/68 |
| 4,717,717 | 1/1988 | Finkenaur | 514/21 |
| 4,742,003 | 5/1988 | Derynck et al. | 435/68 |
| 4,743,679 | 5/1988 | Cohen et al. | 530/350 |
| 4,801,456 | 1/1989 | Drengler | 424/422 |
| 4,806,621 | 2/1989 | Kohn et al. | 528/211 |
| 4,861,757 | 8/1989 | Antoniades et al. | 514/21 |
| 4,874,746 | 10/1989 | Antoniades et al. | 514/21 |
| 4,906,474 | 3/1990 | Langer et al. | 424/428 |
| 4,911,908 | 3/1990 | Estis et al. | 424/857 |
| 4,913,903 | 4/1990 | Sudmann et al. | 424/426 |
| 4,916,193 | 4/1990 | Tang | 525/413 |
| 4,917,685 | 4/1990 | Viswanathan et al. | 604/891.1 |
| 4,929,442 | 5/1990 | Powell | 424/85.2 |
| 4,935,237 | 6/1990 | Higgins et al. | 424/94.64 |
| 4,944,948 | 7/1990 | Uster et al. | 424/450 |
| 4,960,423 | 10/1990 | Smith | 623/1 |
| 4,991,574 | 2/1991 | Pocknell | 128/156 |
| 4,997,425 | 5/1991 | Shiota | 104/304 |

STERILIZATION OF GROWTH FACTORS

This is a continuation of application Ser. No. 07/970,597 filed Oct. 30, 1992, now abandoned, which is a continuation of application Ser. No. 07/801,620 filed Dec. 3, 1991, now abandoned, which is a continuation of application Ser. No. 07/640,910 filed Jan. 11, 1991, now abandoned, which is a continuation-in-part of then application Ser. No. 07/395,476 filed Aug. 18, 1989, now abandoned, which is a continuation-in-part of application Ser. No. 07/529,740 filed May 22, 1990, now issued as U.S. Pat. No. 5,037,429, which is a continuation of application Ser. No. 07/089,735 filed Aug. 26, 1987, now abandoned, and a continuation-in-part of application Ser. No. 07/221,308 filed Jul. 19, 1988, now issued as U.S. Pat. No. 5,051,272, and a continuation-in-part of application Ser. No. 07/397,405 filed Aug. 23, 1989, now abandoned.

BACKGROUND OF THE INVENTION

This invention relates to Human Growth Factors (HGFs) and, more particularly, to the sterilization of therapeutic compositions and surgical articles such as ligatures, hemostatic clips, prosthetic implants, etc., containing one or more HGFs in which ethylene oxide gas is employed as the sterilizant.

HGFs are polypeptides which are known to beneficially affect the wound healing process. See, e.g., Brown et al., "Acceleration of Tensile Strength of Incisions Treated with EGF and TGF-beta", *Ann. Surg.*, pp 788 et seq (Dec. 1988) and Barbul, et al., eds., "Growth Factors and Other Aspects of Wound Healing/Biological and Clinical Implications", *Proceedings Of the Second International Symposium on Tissue Repair*, Tarpon Springs, Fla., May 13–17, 1987 (Alan R. Liss, Inc., New York). Individual HGFs include Human Epidermal Growth Factor (hEGF), Transforming Growth Factor-Beta (TGF-beta), Insulin-like Growth Factor (IGF), Platelet-derived Growth Factor (PDGF) and Fibroblast Growth Factor (FGF).

HGFs are known to be fairly susceptible to degradation. This tendency presents practical difficulties when it is desired to effect their sterilization without, however, negatively affecting their biopotency to an excessive degree. Like most proteinaceous materials, HGFs are heat labile thus ruling out thermal treatments as practical ways to achieve their sterilization. While the use of cold sterilization techniques employing ethylene oxide gaseous compositions has been known for years, the bactericidal action of ethylene oxide is thought to involve a chemical alteration of bacterial proteins, namely through ethoxylation, which accounts for the resulting sterilization. Apparently aware of this, workers in the field have thus far refrained from even investigating the use of ethylene oxide for the sterilization of HGFs.

To date, the prior art has provided little guidance to those concerned with the problem of achieving a practical and effective procedure for sterilizing HGFs. U.S. Pat. No. 3,917,824 indicates that the use of a sterilizing membrane filtration system, e.g., a 0.22 mµ Millipore® filter, a procedure which avoids elevated temperatures and highly reactive chemical sterilizants, is effective for the sterilization of EGFs. However, such a procedure can be impractical for practice on all but a laboratory scale and in any event, cannot be practiced after the EGF has been formulated into a dosage form or has been applied to a solid substrate, e.g., a suture.

SUMMARY OF THE INVENTION

It is a principal object of the invention to provide a process for the sterilization of HGFs, therapeutic compositions containing an HGF and medical and surgical devices filled with an HGF-containing composition employing an ethylene oxide gaseous sterilizant.

It is a further object of the invention to provide for the stabilization of ethylene oxide-sterilized HGFs from excessive loss of biopotency during storage.

In keeping with these and other objects of the invention, a process for the sterilization of an HGF is provided which comprises contacting the HGF with a gaseous sterilizant containing ethylene oxide under conditions resulting in the sterilization of the HGF.

Contrary to expectation, sterilization of HGFs with ethylene oxide has been found not to significantly adversely affect their biopotency. Accordingly, sterilization of HGFs, pharmaceutical compositions containing HGFs, e.g., those formulated as liquids, tablets, capsules, ointments, creams, etc., and surgical articles such as bandages, gauze pads, sutures, surgical staples, hemostatic clips, prosthetic implants, etc., possessing one or more HGFs, can be readily and effectively sterilized with an ethylene oxide-containing gas. Such sterilization is well suited to commercial scale requirements and can be carried out upon HGF-containing medical or surgical articles during their packaging. Thus, e.g., a surgical suture possessing an HGF component to promote or accelerate healing of the surgical incision can be readily sterilized with ethylene oxide within its package. The use of membrane filtration techniques to achieve sterilization of HGFs as disclosed in U.S. Pat. No. 3,917,824 referred to above is, of course, unsuitable for effecting in-package sterilization of HGFs, a limitation to which the ethylene oxide sterilization procedure of this invention is not subject.

DESCRIPTION OF THE PREFERRED EMBODIMENTS

The term "Human Growth Factor" or "HGF" embraces those materials, known in the literature, which are referred to as such and includes their biologically active closely related derivatives. The HGFs can be derived from naturally occurring sources and are preferably produced by recombinant DNA techniques. Specifically, any of the HGFs which are mitogenically active and as such are effective in stimulating, accelerating, potentiating or otherwise enhancing the wound healing process are useful herein, e.g., HEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497, 3,917,824, 3,948,875, 4,338,397, 4,418,691, 4,528,186, 4,621,052, 4,743,679 and 4,717,717, European Patent Applications 0 046 039, 0 128 733, 0 131 868, 0 136 490, 0 147 178, 0 150 572, 0 177 915 and 0 267 016, PCT International Applications WO 83/04030, WO 85/00369, WO 85/01284 and WO 86/02271 and UK Patent Applications GB 2 092 155 A, 2,162,851 A and GB 2 172 890 A, the U.S. patents of which are incorporated by reference herein.

The ethylene oxide sterilization process of this invention can be applied to an essentially pure HGF or mixture of HGFs. More commonly, however, the sterilization process will be carried out upon a therapeutic composition containing one or more HGFs as active ingredient(s). The HGF-containing composition can be formulated for topical or internal application in any of the usual dosage forms, e.g., solution, suspension, dispersion, lyophilizate, gel, cream, paste, powder, ointment, salve, spray, foam, etc., depending on the particular application.

The HGF can be combined with a pharmaceutically acceptable stabilizing agent which protects the sterilized HGF from excessive degradation or loss of biopotency during storage. Stabilizing agents which are suitable for use in the HGF-containing therapeutic compositions are substantially water soluble, liquid polyhydroxy compounds and/or their esters. The expression "liquid polyhydroxy compound" contemplates those polyhydroxy compounds which in the essentially pure state are liquids, as opposed to solids, at or about ambient temperature, e.g., from about 15° C. to about 40° C. The preferred polyhydroxy compounds possess up to about 12 carbon atoms and where their esters are concerned, are preferably the monoesters and diesters. Specific stabilizing agents which can be used with generally good results are glycerol and its monoesters and diesters derived form low molecular weight carboxylic acids, e.g., monacetin and diacetin (respectively, glyceryl monoacetate and glyceryl diacetate), ethylene glycol, diethylene glycol, triethylene glycol, 1,2-propanediol, trimethylolethane, trimethylolpropane, pentaerythritol, sorbitol, and the like.

Glycerol is especially preferred. Mixtures of the aforediscussed polyhydroxy compounds or esters, e.g., sorbitol dissolved in glycerol, glycerol combined with monoacetain and/or diacetin, etc., are also useful.

When the stabilizing agent is of relatively low viscosity (such as may be the case with glycerol), it can be advantageous to include a thickening agent. Many kinds of pharmaceutically acceptable thickeners can be utilized for such purpose including water-soluble polysaccharides, e.g., hydroxypropyl methylcellulose (HPMC), and the other materials of this type which are disclosed in European Patent Application 0 266 015 referred to above, polysaccharide gums such as guar, xanthan, and the like, gelatin, collagen, etc., with or without an aqueous vehicle or other solubilizing agent. An especially preferred class of thickeners are the saturated aliphatic hydroxycarboxylic acids of up to 6 carbon atoms and the alkali metal and alkaline earth metal salts and hydrates thereof.

Within this preferred class of thickeners, an especially preferred class of compounds are those corresponding to the general formula

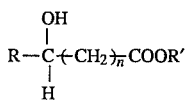

wherein R is hydrogen or methyl, R' is a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinabove, hydrates of these compounds can also be used. Calcium lactate, especially calcium lactate pentahydrate, is a particularly preferred thickener.

Where the use of a thickener is desired, it will be utilized in at least that amount required to increase the overall viscosity of the stabilizing agent to the point where the latter is no longer readily flowable. In the case of a preferred stabilizing agent-thickener combination, namely, glycerol and calcium lactate, the weight ratio of glycerol to calcium lactate can vary from about 1:1 to about 10:1 and preferably is about 7:1.

If desired, the stabilizing agent, and if present, optional thickener, can be dissolved in any suitable solvent or combination of solvents prior to combining with the HGF. To be suitable, the solvent must (1) be miscible with the stabilizing agent or stabilizing agent-thickener combination at the concentration of these components, (2) have a sufficiently high vapor pressure to be readily removed by evaporation, (3) not appreciably affect the efficacy or stability of the HGF. Applying these criteria to a preferred stabilizing agent-thickener combination, namely, an admixture of glycerol and calcium lactate, water and lower alcohols such as methanol and ethanol are entirely suitable solvents.

The HGFs can also contain one or more additional components which promote or enhance the mitogenic activity of the HGF component and/or its effectiveness in accelerating or potentiating the wound healing process. Thus, e.g., site-specific hybrid proteins can be incorporated in the therapeutic composition to maximize the bioavailability of the HGF. See, e.g., Tomlinson (Ciba-Geigy Pharmaceuticals, West Sussex, U.K.), "Selective Delivery and Targeting of Therapeutic Proteins", a paper presented at a symposium held Jun. 12–14, 1989 in Boston, Mass., the contents of which are incorporated by reference herein. The HGFs can also be associated with carrier proteins, e.g., in the form of carrier protein-bound HGF(s), to further enhance the bioavailability of the HGF(s) as disclosed in "Carrier Protein-Based Delivery of Protein Pharmaceuticals", a paper of BioGrowth, Inc , Richmond, Calif. presented at the aforementioned symposium, the contents of said paper being incorporated by reference herein. The HGFs can also be incorporated in liposomes to provide for their release over an extended period. Lactate ion can be present to augment the therapeutic activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl) methacrylamide (HPMA). The HGF can also be combined with one or more antimicrobial agents such as any of the broad spectrum antibiotics (gentamycin sulfate, erythromycin or derivatized glycoproteins), antiseptics, magainin, bone morphogenic protein, tissue or kidney plasminogen activator to cause thrombosis, enzymes such as superoxide dismutase to scavenge tissue-damaging free radicals, tumor necrosis factor for cancer therapy, colony stimulating factor, interferon, interleukin-2 or other lymphokine to enhance the immune system, and so forth.

The amounts of HGF, stabilizing agent and optional component(s) such as thickener, site specific hybrid protein, carrier protein, etc., identified above which may be incorporated in the HGF-containing composition can vary widely and in general will be at least that amount of a particular component which is required to perform its respective function in an effective way. Those skilled in the art employing known or conventional procedures can readily determine optimum amounts of each component for a particular therapeutic composition and therapeutic application.

In general, the HGF(s) must be present in the composition in at least a mitogenically active amount. In many cases the total amount of HGF(s) present in the composition can range from about 0.1 to about 25,000 micrograms per gram of such composition, preferably from about 0.5 to about 10,000 micrograms per gram of composition and most preferably from about 1 to about 500 micrograms per gram of composition.

As previously indicated, the ethylene oxide sterilization process of this invention can also be applied to a medical or surgical device which has been filled with an HGF-containing composition such as any of those previously mentioned. The term "filled" refers to the association of the medical or surgical device with the HGF-containing composition whether this association be one in which the composition or any portion or component(s) thereof is absorbed by the surgical device and/or is present on the surface of the device. Medical and surgical devices which are filled with an HGF-containing composition and thereafter sterilized with ethylene oxide in accordance with this invention include externally applied devices such as pads, patches, swabs, gauze, bandages, and other types of wound dressings, and implantable devices such as sutures, surgical staples, hemostatic clips, prosthetic devices, grafts, and the like. Application of the HGF-containing composition to the medical or surgical device can be carried out in any number of ways. Thus, for example, the device can be submerged in the composition until it acquires at least a wound healing enhancing amount of the composition, even after the optional removal of any excess agent and/or accompanying solvent (if present) such as by drainage wiping, evaporation, etc. In many cases, contact times on the order of from just a few seconds, e.g., about 10 seconds or so, to several hours, e.g., about 2 hours and even longer, are sufficient to impart an effective amount of the filling composition to the device. This method of contacting the implantable surgical device with HGF-containing composition can be conducted continuously or in batch. Thus, in the case of a suture, a running length of the suture can be continuously passed through a quantity of the HGF-containing composition at a velocity which has been previously determined to provide the necessary degree of exposure, or contact time, of the suture with the composition. As the suture emerges from the composition, it can be passed through a wiper or similar device to remove excess filling material prior to the packaging operation. In a batch operation, a quantity of suture is merely submerged within the composition for the requisite period of time with any excess agent being removed form the suture if desired.

Alternatively the HGF-containing composition and solutions thereof can be applied by spraying, brushing, wiping, etc., on the surfaces of the medical or surgical device such that the device will receive and retain at least an effective amount of the composition. Yet another procedure which can be used to apply the HGF-containing composition involves inserting the medical or surgical device, e.g., a suture, in a package containing an effective amount of the composition such that intimate contact between the device and the composition will be achieved.

Where the device to be sterilized is an implantable surgical device of the bioabsorbable variety, e.g., a braided suture manufactured from a bioabsorbable polymer such as a homopolymer or copolymer of glycolide, lactide, etc., it is preferred that the HGF-containing composition contain a liquid polyhydroxy compound since such compound not only functions to stabilize the HGF from excessive loss of biopotency during storage, it further functions to stabilize the surgical device from excessive loss of in vivo tensile strength which might otherwise result from relatively long term exposure of the device to the hydrolytic action of water vapor. Where, as previously mentioned, the liquid polyhyroxy compound is a fairly low viscosity material such as glycerol, a thickener such as any of those recited above is also advantageously present in the HGF-containing composition. It is preferred that the HGF-containing composition with it liquid polyhydroxy stabilizing component and optional thickener component be applied to the bioabsorbable surgical device when the moisture level of the device has equilibrated to that of the surrounding atmosphere, e.g., from about 5 percent to about 40 percent relative humidity or even higher. Such a moisture content in the atmosphere will typically result in the device possessing an amount of moisture in the range of from about 0.3 to about 1.5 weight percent or more.

It can also be advantageous to apply one or more coating compositions to the HGF-filled implantable surgical device prior to its sterilization where particular functional properties of the device are desired. Thus, for example, in the case or a bioabsorbable suture which includes an HGF-stabilizing agent such as glycerol, the suture can be coated with a polyethylene oxide-polypropylene oxide block copolymer or polyalkylene glycol, either of which has been further polymerized with glycolide monomer and lactide monomer or glycolide/lactide copolymer to improve surface lubricity and facilitate knot tie-down.

The sterilization process of this invention contemplates the use of known and conventional ethylene oxide-containing gases and sterilization equipment and conditions, e.g., as described in Kirk-Othmer, "Encyclopedia of Chemical Technology", 3rd ed., Vol. 21, pp. 637–638 and the substantial body of patent and non-patent literature on the subject. Typically, the ethylene oxide is diluted with a non-flammable gas such as carbon dioxide or a fluorocarbon gas such as dichlorodifluoromethane (Freon® 12 of DuPont) for safer handling. Mixtures of 12 volume percent ethylene oxide and 88 volume percent Freon 12 are commonly used. The critical parameters of ethylene oxide sterilization are temperature (e.g., from about 75 to about 140° F., and preferably from about 85 to about 95° C.), time (e.g., from about 2 to about 12 hours, and preferably from about 6 to about 10 hours), concentration of ethylene oxide (e.g., from about 300 to about 1200 mg/l and preferably from about 400 to 1000 mg/l) and relative humidity (e.g., from about 30 to about 80, and preferably from about 40 to about 70 percent).

A conditioning step may optionally be included before the sterilization process discussed above. For example, the HGF-containing therapeutic compositions and/or surgical articles may first be exposed to an environment having a relative humidity of from about 40 to about 50% at a temperature of from about 65 to about 100° F. for a period of two to twelve hours. Conditioning serves to prepare the compositions or articles for the sterilization process, thereby permitting the sterilizant to act most efficiently and effectively.

Known and conventional techniques of analysis are contemplated for measuring the bioburden of the HGF-containing composition or HGF-filled medical or surgical device for the purpose of establishing the specific operational parameters of a particular sterilization cycle. When sterilization is carried out upon the HGF, HGF-containing composition or HGF-filled medical or surgical device in the package, following the sterilization procedure the package, at least part of which is constructed of a material which permits the transmission of ethylene oxide gas, is transferred to a vacuum chamber for removal of residual ethylene oxide gas, e.g., at a temperature of from about 85 to about 100° F. and a relative humidity of less than about 30% for a period of time sufficient to allow residual ethylene oxide levels to drop to a sufficiently low level, e.g., less than about 220 ppm.

The following example is illustrative of the process for the ethylene oxide sterilization of HGFs in accordance with the present invention.

EXAMPLE 1

A. Preparation of HEGF-Filled Bioabsorbable Suture

A solution of glycerol stabilizing agent (278 gm), calcium lactate, thickeners (43 gm) and sterile water (370 gm) was prepared. Human Growth Factor HEGF-51 (152.6 mg) (Creative Biomolecules, Inc., Hopkinton, Mass.) was dissolved volumetrically to 25 mL with the above solution to provide an HGF-containing composition. The composition was placed in the syringe pump of a braided suture coating apparatus. The syringe pump was set to provide the filling composition at a constant rate and the braided suture speed was adjusted to apply 17 mL of filling composition to 200 meters of braid traveling at a braid speed of 43.9 meters/min. The suture was a size 0 braided suture fabricated from a glycolide-lactide copolymer based on 90 weight percent glycolide and 10 weight percent lactide. The target concentration of hEGF on the braid was 0.52 mg hEGF/meter or approximately 1.8 mg hEGF/gram of braid. After filling, the braid was immediately passed through a 50° C. drying column.

After filling, the spooled braid was removed to a small chamber and stored under a flowing dry nitrogen atmosphere to remove the water from the solution. Samples of both solution and filled braid were analyzed by liquid chromatography. The solution was found to be 98% active and the filled braided suture was found to be active with hEGF measuring slightly above target.

The bioburden of the hEGF-filled suture was less than 5.

B. Sterilization of the hEGF-Filled Bioabsorbable Suture

Prior to being placed in an aluminum foil-containing laminated pouch, the suture was subjected to preconditioning in an environment maintained at 40–50% relative humidity at 70°–74° F. for a minimum of twelve hours. After being placed in the foil pouch, the open pouch was placed in an outer "breather" package impervious to microbes but permitting transfer of ethylene oxide through its Tyvek® panel. The outer, but not the inner, package was sealed and placed in the sterilizer unit which was operated with a mixture of 12 volume percent ethylene oxide (ETO) and 88 volume percent Freon 12. Sterilization of the package and its contents was carried out under the conditions set forth in the Table as follows:

TABLE

Sterilization Conditions

| Parameter | Units | Setting |
|---|---|---|
| Gas Charging Step | | |
| Elapsed Time | Minutes | 20 ± 10 |
| Relative Humidity | % | 40–70 |
| Gas Weight Used | lbs. | 232 Minimum |
| Sterilization | | |
| Temperature | °F. | 90.0 ± 5.0 |
| Pressure | PSI | 1.3 ± 0.3 |
| Relative Humidity | % | 40–70 |
| Time at Temperature | Hrs:Min | 8:00 Minimum |
| Total Exposure Time | Hrs:Min | 10:00 |
| Initial ETO Content | mg/l | 400–600 |
| Final Gas Weight | lbs. | ≦325 |
| Exhaust | | |
| First Vacuum | In Hg | 25.5 ± 2 |
| First Elapsed Time | Minutes | 20 Minimum |
| Second Vacuum | In Hg | 25.5 ± 2 |
| Second Elapsed Time | Minutes | 20 Minimum |

Following sterilization, the package was removed from the sterilization unit to an environment maintained at 30% relative humidity and 87°–93° F. to reduce residual ethylene oxide content still further, i.e., to below 200 ppm. Subsequent analyses of the sterilized suture indicated the suture to be sterile and the hEGF to be essentially as active as prior to sterilization.

EXAMPLE 2

Four growth factors, namely IGF, PDGF, FGF and hEGF, were lyophilized with bovine albumin at a concentration of 50 ug of growth factor per 5 mg of bovine albumin for the IGF, PDGF and hEGF, and at a concentration of 40 ug of growth factor per 5 mg of bovine albumin for the FGF, to form lyophilized powders. The powders were placed in sterilization pouches having one wall fabricated from DuPont Tyvek 1073B (8 mils) and the opposing wall made from DuPont polypropylene 1948-20 (2 mils). The lyophilized powder-containing pouches were placed in a sterilization chamber and sterilized according to the sterilization conditions set forth in the Table, Supra. Subsequent analyses of the lyophilized powders showed that the powders were sterile and that the growth factors maintained their biological activities.

EXAMPLE 3

Four growth factors, namely IGF, PDGF, FGF and hEGF, were immobilized on Immobilon, a polyvinylidene difluoride membrane from Millipore, at a concentration of 50 ug of growth factor per 3 cm×2 cm area of membrane. The membranes were placed in sterilization pouches of the type used in Example 2 and the pouches were placed in a sterilization chamber. The samples were sterilized according to the sterilization conditions set forth in the Table, supra. Subsequent analyses of the growth factors (after being eluted from the membranes) showed that the samples were sterile and that the growth factors maintained their biological activities.

What is claimed is:

1. A process for the sterilization of an article selected from the group consisting of a suture, pad, patch, swab, gauze, bandage, surgical staple, hemostatic clip, prosthetic device and graft, said article containing or filled with a human epidermal growth factor-containing composition of calcium lactate and a member selected from the group consisting of glycerol and sorbitol dissolved in glycerol which comprises contacting the human epidermal growth factor with a gaseous sterilizant containing a concentration of from about 300 to about 1200 mg/l of ethylene oxide under conditions resulting in the sterilization of the human epidermal growth factor and stabilization of the same against loss of biopotency during storage, wherein sterilization is carried out at a temperature of from about 75° to about 140° F. for a period of from about 2 to about 12 hours, an ethylene oxide concentration of from about 300 to about 1200 mg/l and a relative humidity of from about 30 to about 80 percent.

2. The process of claim 1 wherein said suture is a bioabsorbable suture.

3. The process of claim 1 wherein sterilization is carried out at a temperature of from about 85° to about 95° F. for a period of from about 6 to about 10 hours, an ethylene oxide concentration of from about 400 to about 1000 mg/l and a relative humidity of from about 40 to about 70 percent.

* * * * *